(12) United States Patent
Jan et al.

(10) Patent No.: US 8,853,481 B2
(45) Date of Patent: Oct. 7, 2014

(54) HIGHLY SELECTIVE ALKYLATION PROCESS WITH LOW ZEOLITE CATALYST COMPOSITION

(71) Applicant: UOP LLC, Des Plaines, IL (US)

(72) Inventors: Deng-Yang Jan, Elk Grove Village, IL (US); Robert J. Schmidt, Barrington, IL (US); Pelin Cox, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/661,200

(22) Filed: Oct. 26, 2012

(65) Prior Publication Data

US 2014/0121431 A1    May 1, 2014

(51) Int. Cl.
*C07C 2/66* (2006.01)

(52) U.S. Cl.
USPC .......................... 585/467; 585/448; 585/449

(58) Field of Classification Search
USPC ........................................ 585/467, 449, 448
See application file for complete search history.

(56) References Cited

U.S. PATENT DOCUMENTS

| | | | |
|---|---|---|---|
| 5,942,650 A | 8/1999 | Gajda | |
| 6,756,030 B1 | 6/2004 | Rohde et al. | |
| 7,019,185 B2 | 3/2006 | Dandekar et al. | |
| 7,091,390 B2 | 8/2006 | Jan et al. | |
| 7,268,267 B2 | 9/2007 | Jan et al. | |
| 7,348,465 B2 | 3/2008 | Murray et al. | |
| 7,632,974 B2 | 12/2009 | Schwint | |
| 7,638,667 B2 | 12/2009 | Jan et al. | |
| 7,939,700 B2 | 5/2011 | Clark et al. | |
| 2003/0102267 A1 | 6/2003 | Kim et al. | |
| 2004/0199036 A1 | 10/2004 | Jan et al. | |
| 2008/0194893 A1 | 8/2008 | Sohn et al. | |
| 2009/0182182 A1 | 7/2009 | Bauer | |
| 2010/0280298 A1 | 11/2010 | Clark et al. | |
| 2011/0077442 A1 * | 3/2011 | Jan et al. | 585/455 |
| 2011/0245558 A1 | 10/2011 | Schmidt | |

FOREIGN PATENT DOCUMENTS

| | | |
|---|---|---|
| WO | WO 02/051801 A1 | 7/2002 |
| WO | WO 03/074452 A1 | 9/2003 |
| WO | WO 2011/146171 A2 | 11/2011 |

* cited by examiner

*Primary Examiner* — Thuan D Dang
(74) *Attorney, Agent, or Firm* — Mark R Willis

(57) ABSTRACT

A method for alkylation of a feedstock is described. The method includes contacting the feedstock comprising at least one alkylatable aromatic compound and an alkylating agent with a first alkylating catalyst composition under alkylating conditions, the first alkylating catalyst composition comprising UZM-8 zeolite and a binder, the first alkylating catalyst composition having less than 50 wt% UZM-8 zeolite; wherein a total alkylated selectivity at a temperature and a molar ratio of alkylatable aromatic compound to alkylating agent is greater than 99.0%.

16 Claims, 1 Drawing Sheet

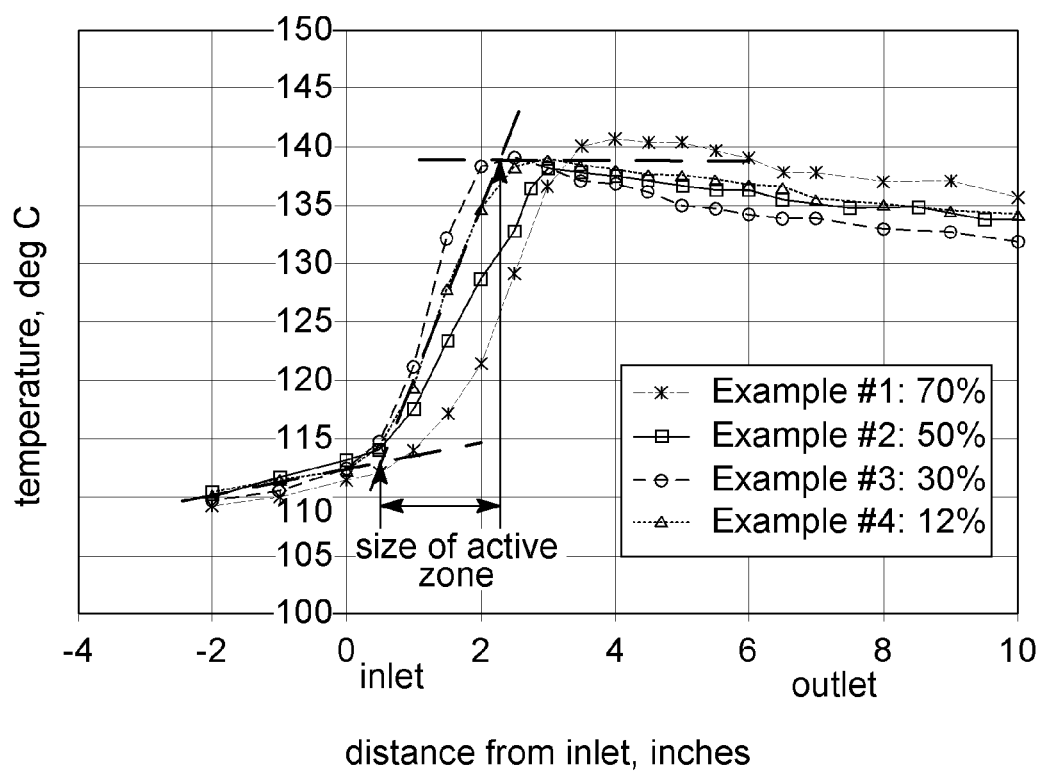

HIGHLY SELECTIVE ALKYLATION PROCESS WITH LOW ZEOLITE CATALYST COMPOSITION

FIELD OF THE INVENTION

The present invention relates to a process for alkylation of a feedstock, and more specifically to a highly active, stable and selective alkylation process with a low zeolite catalyst composition.

BACKGROUND OF THE INVENTION

Alkylation of aromatic compounds with a $C_2$ to $C_4$ olefin and transalkylation of polyalkylaromatic compounds are two common reactions for producing monoalkylated aromatic compounds. Examples of these two reactions that are practiced industrially to produce ethylbenzene are the alkylation of benzene with ethylene and the transalkylation of benzene and diethylbenzene.

Combining alkylation and transalkylation can thus maximize ethylbenzene production. Such a combination can be carried out in a process having two reaction zones, one for alkylation and the other for transalkylation, or in a process having a single reaction zone in which alkylation and transalkylation both occur.

A key operating variable directly related to operating efficiency of alkylation process is the molar ratio of aryl groups per alkyl group. The lower the ratios, the lower the amounts of benzene required to recover/recycle, the lower the capital and utility cost would be. The numerator of this ratio is the number of moles of aryl groups passing through the reaction zone during a specified period of time. The number of moles of aryl groups is the sum of all aryl groups, regardless of the compound in which the aryl group happens to be. In the context of ethylbenzene production, for example, one mole of benzene, one mole of ethylbenzene, and one mole of diethylbenzene each contribute one mole of aryl group to the sum of aryl groups. The denominator of this ratio is the number of moles of alkyl groups that have the same number of carbon atoms as that of the alkyl group on the desired monoalkylated aromatic and which pass through the reaction zone during the same specified period of time. The number of moles of alkyl groups is the sum of all alkyl and alkenyl groups with the same number of carbon atoms as that of the alkyl group on the desired monoalkylated aromatic, regardless of the compound in which the alkyl or alkenyl group happens to be, except that paraffins are not included. In the context of ethylbenzene production, the number of moles of ethyl groups is the sum of all ethyl and ethenyl groups, regardless of the compound in which the ethyl or ethenyl group happens to be, except that paraffins, such as ethane, propane, n-butane, isobutane, pentanes, and higher paraffins are excluded from the computation of the number of moles of ethyl groups. For example, one mole of ethylene and one mole of ethylbenzene each contribute one mole of ethyl group to the sum of ethyl groups, whereas one mole of diethylbenzene contributes two moles of ethyl groups and one mole of triethylbenzene contributes three moles of ethyl groups. Butylbenzene and octylbenzene contribute no moles of ethyl groups Advancements in zeolites and catalysts have enabled the aromatic alkylation process to operate at lower aryl to alkyl ratios. The catalysts typically include a relatively high content of zeolite in order to ensure good activity, activity stability and stable long-term operation. Currently, aromatic alkylation catalysts including UZM-8 zeolite have a zeolite content greater than 50 wt %.

Zeolite is synthesized using organic templates, which are removed via calcinations in the catalyst preparation. Because of the heat and steam evolved during the calcination, the zeolite would incur appreciable structural and framework damages. The degree of damage is related to the degree of hydrothermal severity, which is proportional to the amount of the zeolite in the catalyst. Furthermore, at high zeolite contents, the zeolite in the catalyst tends to agglomerate, reducing the effective utilization of zeolite. Lastly because of the high cost of zeolites, catalysts containing high levels of zeolites and processes using those catalysts are also expensive.

SUMMARY OF THE INVENTION

One aspect of the invention is a method for alkylation of a feedstock. In one embodiment, the method includes contacting the feedstock comprising at least one alkylatable aromatic compound and an alkylating agent with a first alkylating catalyst composition under alkylating conditions, the first alkylating catalyst composition comprising UZM-8 zeolite and a binder, the first alkylating catalyst composition having less than 50 wt % UZM-8 zeolite; wherein a total alkylated selectivity at a temperature and a molar ratio of alkylatable aromatic compound to alkylating agent is greater than 99.0%.

BRIEF DESCRIPTION OF THE DRAWING

The Figure is a graph showing the effect of zeolite content on catalyst activity measured by the position of the end of the active zone (EAZ).

DETAILED DESCRIPTION OF THE INVENTION

To ensure high olefin conversion, maintain activity stability, and attain high alkylated product selectivity and long-term operating stability, the alkylation catalyst typically contains a zeolite content of greater than 50%. The activity is measured as olefin conversion determined by the amount of olefin at the reactor inlet and that unconverted at the outlet of the reactor. Alternatively the catalyst activity is measured by the size of the active zone required to reach to maximal temperatures, and the activity stability is measured by the stability of the size of the active zone as a function of time on stream. In commercial operation, the size of the active zone is a fraction of the total catalyst bed in a fixed bed reactor, while the remaining catalyst bed functions as the catalyst life zone. It is advantageous to have a highly active catalyst, which ensures a minimal size of the active zone and maximal life zone to attain long-term stable operation. The active zone should be no more than 50% of the overall catalyst bed. Total alkylated selectivity is defined as the production of mono- and poly-alkylated benzene out of the total benzene and olefin consumed on a carbon basis. The total alkylated selectivity represents the possibly maximal amounts of recoverable alkylated products through the alkylation and trans-alkylation reactor, a measurement of the efficiency of feed utilization. Again, to maintain a long-term stable and efficient commercial production of cumene, a minimal amount of zeolite is required.

It was unexpectedly found that the alkylation catalysts containing significantly less than 50% UZM-8 zeolite maintained high activity and activity stability under process conditions of low benzene to olefin ratios and temperatures, which are severe but economically advantageous. The activity measured on the basis of olefin conversions remains unchanged, when the zeolite contents of the catalyst are reduced to very low amounts. Most unexpectedly the activity measured by the size of EAZ remains unchanged. It is also unexpectedly found that the total alkylated product selectivity remains unchanged with catalysts containing very low UZM-8 zeolite contents. For example, the total alkylated selectivity can be greater than 99.0%, or greater than 99.1%, or greater than 99.2%, or greater than 99.3%, or greater than 99.4%, or greater than 99.5%, or greater than 99.6%, or greater than 99.7%.

In one embodiment of the invention the alkylation reactor is made up entirely of a catalyst containing less than 50 wt % UZM-8 zeolite at a given temperature and molar ratio of aromatic compound to alkylating agent. The alkylation catalyst comprises a UZM-8 zeolite and a binder. The zeolite is present in an amount of at least 1 wt % and less than 50 wt % of the catalyst composition, with the remainder being the binder. There can be less than about 40 wt % zeolite, or less than about 30 wt % zeolite, or less than about 25 wt % zeolite, or less than about 20 wt % zeolite, or less than about 15 wt % zeolite, or less than about 10 wt % zeolite, or about 2 wt to about 10 wt % zeolite. The binder comprises one or more conventional zeolite binder materials such as those described below.

In another embodiment of the invention, the alkylation reactor is made up of two catalysts with the lead catalyst containing less than 50 wt % UZM-8 zeolite and the lag catalyst containing greater than 50 wt % UZM-8 zeolite. The lead alkylation catalyst comprises a UZM-8 zeolite and a binder with the zeolite present in an amount of at least 1 wt % and less than 50 wt % of the catalyst composition, with the remainder being the binder.

There can be less than about 40 wt % zeolite, or less than about 30 wt % zeolite, or less than about 25 wt % zeolite, or less than about 20 wt % zeolite, or less than about 15 wt % zeolite, or less than about 10 wt % zeolite, or about 2 wt to about 10 wt % zeolite. The binder comprises one or more conventional zeolite binder materials such as those described below. The lag catalyst contains greater than 50 wt % UZM-8 zeolite with the balance comprising one or more conventional binder materials such as those described below. In this embodiment, the catalyst containing less than 50 wt % UZM-8 zeolite is made up of at least about 30% and preferably at least about 50% of the alkylator reactor with the balance being catalyst containing more than 50 wt % of UZM-8 zeolite.

In ethyl benzene (EB), cumene, and heavier alkylates such as linear alkylbenzenes used in the manufacture of detergents, lower UZM-8 zeolite content maintains high catalyst activity, activity stability and total alkylate selectivity. As the zeolite content was reduced, the catalysts did not show debits in activity, activity stability or total alkylated selectivity based on the amounts of benzene and propylene converted on a carbon basis. The catalyst showed greater than 90% propylene conversion and stable activity at relatively severe conditions of low inlet temperatures and low benzene to olefin ratios for zeolite contents greater than 2 wt %. This is in comparison to normal processing conditions of greater than 90% conversion achieved at 130° C. and a much higher zeolite content of 50% or more. The conversion (e.g., ethylene, propylene, or butene) was typically greater than 90%, or greater than 95%, or greater than 96%, or greater than 97%, or greater than 98%, or greater than 99%.

In another preferred embodiment of the invention, the process comprises the alkylation reactor made up of the catalysts containing less than 50 wt % UZM-8 zeolite contents or a combination of two catalysts with one containing less than 50 wt % and the other containing more than 50 wt % UZM-8 zeolite and guard beds to remove contaminants from the feed streams. The long-term deactivation of UZM-8 based catalysts is typically caused by contaminants, specifically basic nitrogen compounds, oxygen including oxygenates, and highly unsaturated aliphatic hydrocarbons in benzene. Sulfur can also have an impact on activity and/or activity stability on UZM-8 and beta-containing catalysts. Metals, including but not limited to, As, Hg, and Pb, can also impact performance at the low zeolite levels.

By incorporating one or more guard beds to remove oxygenate species, nitrogen and sulfur containing compounds, and/or highly unsaturated aliphatic hydrocarbons and metals, alkylation process with low zeolite contents can be used. The guard bed essentially eliminates contaminants from the benzene feed stream, protecting the alkylation catalyst. The importance of protecting the alkylation catalyst from contaminants increases in importance as the zeolite content decreases because the contaminants can reduce the catalyst activity.

The process significantly reduces the overall cost of the adsorbent and catalyst. The cost of manufacturing the guard bed material is much less than the alkylation catalyst because of the pressurized synthesis of the UZM-8 catalyst.

Suitable guard beds for nitrogen, oxygenates, sulfur containing compounds, and/or highly unsaturated acyclic and cyclic hydrocarbons and metals are known in the art. In one embodiment, the guard bed can utilize an adsorbent made of steamed modified zeolite Y/Al$_2$O$_3$. In another embodiment, the guard bed is made up of Ni—Mo—O on a steamed modified zeolite Y/Al$_2$O$_3$ support. In another embodiment, the adsorbent can be Ni—Mo—O on a cation exchanged zeolite X and Y support with the cations being Mg, Y (yttrium), and rare earth elements. The guard bed can be operated at a temperature in the range of about 25° C. to about 260° C., and a pressure of about 0.71 MPa (100 psig) to about 4.1 MPa (600 psig).

The catalyst for the process disclosed herein contains one or more members of the family of aluminosilicate and substituted aluminosilicate zeolites designated UZM-8 and UZM-8HS, which are described in U.S. Pat. Nos. 6,756,030, 7,091,390, 7,268,267, and 7,638,667, for example, each of which is incorporated herein by reference. U.S. Pat. No. 6,756,030 describes UZM-8 and its preparation, and therefore it is not necessary herein to describe these in detail. Briefly, UZM-8 zeolites are prepared in an alkali-free reaction medium in which only one or more organoammonium species are used as structure directing agents. In this case, the microporous crystalline zeolite (UZM-8) has a composition in the as-synthesized form and on an anhydrous basis expressed by the empirical formula:

$$R_r^{p+}Al_{1-x}E_xSi_yO_z$$

where R is at least one organoammonium cation selected from the group consisting of protonated amines, protonated diamines, quaternary ammonium ions, diquaternary ammonium ions, protonated alkanolamines and quaternized alkanolammonium ions. Preferred organoammonium cations are those that are non-cyclic or those that do not contain a cyclic group as one substituent. Of these those that contain at least two methyl groups as sub stituents are especially preferred. Examples of preferred cations include without limitation DEDMA, ETMA, HM and mixtures thereof. The ratio of R to (Al+E) is represented by "r" which varies from about 0.05 to about 5. The value of "p" which is the weighted average valence of R varies from 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation $$z=(rp+3+4y)/2.$$

The UZM-8 zeolites can be prepared using both organoammonium cations and alkali and/or alkaline earth cations as structure directing agents. As in the alkali-free case above, the same organoammonium cations can be used here. Alkali or alkaline earth cations are observed to speed up the crystallization of UZM-8, often when present in amounts less than 0.05 M$^+$/Si. For the alkali and/or alkaline earth metal containing systems, the microporous crystalline zeolite (UZM-8) has a composition in the as-synthesized form and on an anhydrous basis expressed by the empirical formula:

$$M_m^{n+}R_r^{p+}Al_{1-x}E_xSi_yO_z$$

where M is at least one exchangeable cation and is selected from the group consisting of alkali and alkaline earth metals. Specific examples of the M cations include but are not limited to lithium, sodium, potassium, rubidium, cesium, calcium, strontium, barium and mixtures thereof. Preferred R cations include without limitation DEDMA, ETMA, HM and mixtures thereof. The value of "m" which is the ratio of M to (Al+E) varies from about 0.01 to about 2. The value of "n" which is the weighted average valence of M varies from about 1 to about 2. The ratio of R to (Al+E) is represented by "r" which varies from 0.05 to about 5. The value of "p" which is the weighted average valence of R varies from about 1 to about 2. The ratio of Si to (Al+E) is represented by "y" which varies from about 6.5 to about 35. E is an element which is tetrahedrally coordinated, is present in the framework and is selected from the group consisting of gallium, iron, chromium, indium and boron. The mole fraction of E is represented by "x" and has a value from 0 to about 0.5, while "z" is the mole ratio of O to (Al+E) and is given by the equation $$z=(mn+rp+3+4y)/2$$

where M is only one metal, then the weighted average valence is the valence of that one metal, i.e. +1 or +2. However, when more than one M metal is present, the total amount of $$M_m^{n+}=M_{m1}^{(n1)+}+M_{m2}^{(n2)+}+M_{m3}^{(n3)+}$$

and the weighted average valence "n" is given by the equation:

$$n = \frac{m1 \cdot n1 + m2 \cdot n2 + m3 \cdot n3 + \ldots}{m1 + m2 + m + \ldots}$$

Similarly when only one R organic cation is present, the weighted average valence is the valence of the single R cation, i.e., +1 or +2. When more than one R cation is present, the total amount of R is given by the equation.

$$R_r^{p+}=R_{r1}^{(p1)+}+R_{r2}^{(p2)+}+R_{r3}^{(p3)+}$$

and the weighted average valence "p" is given by the equation $$p = \frac{p1 \cdot r1 + p2 \cdot r2 + p3 \cdot r3 + \ldots}{p1 + p2 + p3 + \ldots}$$

The microporous crystalline zeolites used in the process disclosed herein are prepared by a hydrothermal crystallization of a reaction mixture prepared by combining reactive sources of R, aluminum, silicon and optionally M and E. The sources of aluminum include but are not limited to aluminum alkoxides, precipitated aluminas, aluminum metal, sodium aluminate, organoammonium aluminates, aluminum salts and alumina sols. Specific examples of aluminum alkoxides include, but are not limited to aluminum ortho sec-butoxide and aluminum ortho isopropoxide. Sources of silica include but are not limited to tetraethylorthosilicate, colloidal silica, precipitated silica, alkali silicates and organoammonium silicates. A special reagent consisting of an organoammonium aluminosilicate solution can also serve as the simultaneous source of Al, Si, and R. Sources of the E elements include but are not limited to alkali borates, boric acid, precipitated gallium oxyhydroxide, gallium sulfate, ferric sulfate, ferric chloride, chromium nitrate and indium chloride. Sources of the M metals include the halide salts, nitrate salts, acetate salts, and hydroxides of the respective alkali or alkaline earth metals. R can be introduced as an organoammonium cation or an amine. When R is a quaternary ammonium cation or a quaternized alkanolammonium cation, the sources include but are not limited the hydroxide, chloride, bromide, iodide and fluoride compounds. Specific examples include without limitation DEDMA hydroxide, ETMA hydroxide, tetramethylammonium hydroxide, tetraethylammonium hydroxide, hexamethonium bromide, tetrapropylammonium hydroxide, methylethylammonium hydroxide, tetramethylammonium chloride and choline chloride. R may also be introduced as an amine, diamine, or alkanolamine that subsequently hydrolyzes to form an organoammonium cation. Specific non-limiting examples are N,N,N',N'-tetramethyl-1,6-hexanediamine, triethylamine, and triethanolamine. Preferred sources of R without limitation are ETMAOH, DEDMAOH, and hexamethonium dihydroxide (HM(OH)$_2$).

The reaction mixture containing reactive sources of the desired components can be described in terms of molar ratios of the oxides by the formula:

$$aM_{2/n}O:bR_{2/p}O:1-cAl_2O_3:cE_2O_3:dSiO_2:eH_2O$$

where "a" varies from 0 to about 25, "b" varies from about 1.5 to about 80, "c" varies from 0 to 1.0, "d" varies from about 10 to about 100, and "e" varies from about 100 to about 15000. If alkoxides are used, it is preferred to include a distillation or evaporative step to remove the alcohol hydrolysis products. The reaction mixture is now reacted at a temperature of about 85° C. to about 225° C. (185 to 437° F.) and preferably from about 125° C. to about 150° C. (257 to 302° F.) for a period of about 1 day to about 28 days and preferably for a time of about 5 days to about 14 days in a sealed reaction vessel under autogenous pressure. After crystallization is complete, the solid product is isolated from the heterogeneous mixture by means such as filtration or centrifugation, and then washed with deionized water and dried in air at ambient temperature up to about 100° C. (212° F.).

The UZM-8 aluminosilicate zeolite, which is obtained from the above-described process, is characterized by an x-ray diffraction pattern, having at least the d-spacings and relative intensities set forth in Table A below

TABLE A

| d-Spacings and Relative Intensities for as-synthesized UZM-8 | | |
|---|---|---|
| 2-Θ | d(Å) | I/I$_0$ % |
| 6.40-6.90 | 13.80-12.80 | w-s |
| 6.95-7.42 | 12.70-11.90 | m-s |
| 8.33-9.11 | 10.60-9.70 | w-vs |
| 19.62-20.49 | 4.52-4.33 | m-vs |
| 21.93-22.84 | 4.05-3.89 | m-vs |

TABLE A-continued d-Spacings and Relative Intensities for as-synthesized UZM-8

| 2-Θ | d(Å) | I/I$_0$ % |
|---|---|---|
| 24.71-25.35 | 3.60-3.51 | w-m |
| 25.73-26.35 | 3.46-3.38 | m-vs |

The UZM-8 compositions are stable to at least 600° C. (1112° F.) (and usually at least 700° C. (1292° F.)). The characteristic diffraction lines associated with typical calcined UZM-8 samples are shown below in table B. The as-synthesized form of UZM-8 is expandable with organic cations, indicating a layered structure.

TABLE B d-Spacings and Relative Intensity for Calcined UZM-8

| 2-Θ | d (Å) | I/I$_0$ % |
|---|---|---|
| 4.05-4.60 | 21.80-19.19 | w-m |
| 7.00-7.55 | 12.62-11.70 | m-vs |
| 8.55-9.15 | 10.33-9.66 | w-vs |
| 12.55-13.15 | 7.05-6.73 | w |
| 14.30-14.90 | 6.19-5.94 | m-vs |
| 19.55-20.35 | 4.54-4.36 | w-m |
| 22.35-23.10 | 3.97-3.85 | m-vs |
| 24.95-25.85 | 3.57-3.44 | w-m |
| 25.95-26.75 | 3.43-3.33 | m-s |

An aspect of the UZM-8 synthesis that contributes to some of its unique properties is that it can be synthesized from a homogenous solution. In this chemistry, soluble aluminosilicate precursors condense during digestion to form extremely small crystallites that have a great deal of external surface area and short diffusion paths within the pores of the crystallites. This can affect both adsorption and catalytic properties of the material.

As-synthesized, the UZM-8 material will contain some of the charge balancing cations in its pores. In the case of syntheses from alkali or alkaline earth metal-containing reaction mixtures, some of these cations may be exchangeable cations that can be exchanged for other cations. In the case of organoammonium cations, they can be removed by heating under controlled conditions. In the cases where UZM-8 is prepared in an alkali-free system, the organoammonium cations are best removed by controlled calcination, thus generating the acid form of the zeolite without any intervening ion-exchange steps. The controlled calcination conditions include the calcination conditions described herein below for the composite catalyst, and it may sometimes be desirable to perform the controlled calcination of the zeolite after the zeolite has been combined with a binder. On the other hand, it may sometimes be possible to remove a portion of the organoammonium via ion exchange. In a special case of ion exchange, the ammonium form of UZM-8 may be generated via calcination of the organoammonium form of UZM-8 in an ammonia atmosphere.

The catalyst used in the process disclosed herein preferably contains calcined UZM-8. Calcination of as-synthesized UZM-8 effects changes such as in the x-ray diffraction pattern. The UZM-8 zeolite used in the catalyst used in the process disclosed herein contains preferably less than 0.1 wt-%, more preferably less than 0.05 wt-%, and even more preferably less than 0.02 wt-% of alkali and alkaline earth metals. The alkali or alkaline earth metals can be removed from the as synthesized UZM-8 or calcined as synthesized UZM-8 prior to formulating the zeolite into the catalysts. The alkali or the alkali earth metals can also be removed after the as synthesized UZM-8 or calcined as synthesized UZM-8 zeolite being formulated into the catalyst and calcined. The removal of alkali or alkaline earth elements are performed using ammonium exchange using solutions of 0.1 to 20wt % ammonium salts at temperatures ranging from 20 to 95° C.

For use in the process disclosed herein, the zeolite preferably is mixed with a binder for convenient formation of catalyst particles in a proportion of about 1 to 100 mass zeolite and 0 to 99 mass-% binder, with the zeolite preferably comprising from about 2 to 50 mass-% of the composite. The binder should preferably be porous, have a surface area of about 5 to about 800 m$^2$/g, and be relatively refractory to the conditions utilized in the hydrocarbon conversion process. Non-limiting examples of binders are aluminas, titania, zirconia, zinc oxide, magnesia, boria, silica-alumina, silica-magnesia, chromia-alumina, alumina-boria, silica-zirconia, etc.; silica, silica gel, and clays. Preferred binders are amorphous silica and alumina, including gamma-, eta-, and theta-alumina, with gamma- and eta-alumina being especially preferred.

The zeolite with or without a binder can be formed into various shapes such as pills, pellets, extrudates, spheres, etc. Preferred shapes are extrudates and spheres. Extrudates are prepared by conventional means which involves mixing of zeolite either before or after adding metallic components, with the binder and a suitable peptizing agent to form a homogeneous dough or thick paste having the correct moisture content to allow for the formation of extrudates with acceptable integrity to withstand direct calcination. The dough then is extruded through a die to give the shaped extrudate. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

Spheres can be prepared by the well known oil-drop method which is described in U.S. Pat. No. 2,620,314, which is hereby incorporated herein by reference in its entirety. The method involves dropping a mixture of zeolite, and for example, alumina sol, and gelling agent into an oil bath maintained at elevated temperatures. The droplets of the mixture remain in the oil bath until they set and form hydrogel spheres. The spheres are then continuously withdrawn from the oil bath and typically subjected to specific aging treatments in oil and an ammoniacal solution to further improve their physical characteristics. The resulting aged and gelled particles are then washed and dried at a relatively low temperature of about 50-200° C. (122-392° F.) and subjected to a calcination procedure at a temperature of about 450-700° C. (842-1292° F.) for a period of about 1 to about 20 hours. This treatment effects conversion of the hydrogel to the corresponding alumina matrix.

The catalyst composite is dried at a temperature of from about 100° to about 320° C. (212 to 608° F.) for a period of from about 2 to about 24 or more hours and, usually, calcined at a temperature of from 400° to about 650° C. (752 to 1202° F.) in an air atmosphere for a period of from about 1 to about 20 hours. The calcining in air may be preceded by heating the catalyst composite in nitrogen to the temperature range for calcination and holding the catalyst composite in that temperature range for from about 1 to about 10 hours. A catalyst composite used in the process disclosed herein preferably has an x-ray diffraction pattern having at least the d-spacings and relative intensities set forth in Table B.

The binder used in the catalyst composite for the process disclosed herein preferably contains less alkali and alkaline earth metals than the UZM-8 zeolite used in the catalyst composite, and more preferably contains little or no alkali and alkaline earth metals. Therefore, the catalyst composite has a content of alkali and alkaline earth metals of less than that of the UZM-8 zeolite used in forming the catalyst composite, owing to the binder effectively lowering the alkali and alkaline earth metals content of the catalyst composite as a whole.

The process disclosed herein can be expected to be applicable generally to the alkylation of an alkylation substrate with an alkylation agent. The process disclosed herein is more specifically applicable to the production of an alkyl aromatic by alkylation of a feed aromatic with a feed olefin. Although benzene is the principal feed aromatic of interest, feed aromatics such as alkyl-substituted benzenes, condensed ring systems generally, and alkylated derivatives thereof may be used. Examples of such feed aromatics are toluene, ethylbenzene, propylbenzene, and the like; xylene, mesitylene, methylethylbenzene, and the like; naphthalene, anthracene, phenanthrene, methylnaphthalene, dimethyl-naphthalene, and tetralin. More than one feed aromatic can be used. The feed aromatic may be introduced into an alkylation catalyst bed in one or more aromatic feed stream. Each aromatic feed stream may contain one or more feed aromatics. In addition to the feed aromatic(s), an aromatic feed stream may contain non-aromatics, including but not limited to, saturated and unsaturated cyclic hydrocarbons that have the same, one more, or one less, number of carbon atoms as the feed aromatic. For example, an aromatic feed stream containing benzene may also contain cyclohexane, cycloheptane, cyclohexenes, or cycloheptenes, as well as methylated versions of any of these hydrocarbons, or mixtures thereof. The concentration of each feed aromatic in each aromatic feed stream may range from 0.01 to 100 wt-%.

Feed olefins containing from 2 to 6 carbon atoms are the principal alkylating agents contemplated for the process disclosed herein. Examples of such feed olefins include $C_2$-$C_4$ olefins, namely ethylene, propylene, butene-1, cis-butene-2, trans-butene-2, and iso-butene. However, feed olefins having from 2 to 20 carbon atoms may be used effectively in the process disclosed herein. More than one feed olefin may be used. The feed olefin may be introduced into an alkylation catalyst bed in one or more olefinic feed streams. Each olefinic feed stream may contain one or more feed olefins. In addition to the feed olefin(s), an olefinic feed stream may contain non-olefins, such as paraffins that have the same number of carbon atoms as the olefin. For example, a propylene-containing olefinic feed stream may also contain propane, while an olefinic feed stream containing ethylene may also contain ethane. The concentration of each feed olefin in each olefinic feed stream may range from 0.01 to 100 wt-%.

The most widely practiced hydrocarbon conversion processes to which the present invention is applicable are the catalytic alkylation of benzene with ethylene to produce ethylbenzene, the catalytic alkylation of benzene with propylene to produce cumene, and the catalytic alkylation of benzene with butene to produce butylbenzene. Although the discussion herein of the present invention refers to a catalytic cumene reaction system, the discussion is also in reference to its application to a catalytic ethylbenzene reaction system. It is not intended that this discussion limit the scope of the present invention as set forth in the claims.

In practicing the process disclosed herein, a portion of the effluent of the alkylation reaction zone is reintroduced into the alkylation reaction zone. Unless otherwise noted in this specification, the term "portion," when describing a process stream, refers to either an aliquot portion of the stream or a dissimilar fraction of the stream having a different composition than the total stream from which it was derived. An aliquot portion of the stream is a portion of the stream that has essentially the same composition as the stream from which it was derived. The ratios of the effluent to combined fresh feeds range from 0.5 to 20 and preferably from 1.0 to 10 on a weight basis. Alkylation is preferably performed in either mixed or the liquid phase. Consequently, reaction pressure needs to be sufficiently high to ensure at least a partial liquid phase. Where ethylene is the olefin, the pressure range for the reactions is usually from about 1379 to 6985 kPa(g) (200 to about 1000 psi(g)), more commonly from about 2069 to 4137 kPa (g) (300 to about 600 psi(g)), and even more commonly from about 3103 to 4137 kPa(g) (450 to about 600 psi(g)). Preferably, the reaction conditions are sufficient to maintain benzene in a liquid phase and are supercritical conditions for ethylene. Pressure is not a critical variable in the success of the process disclosed herein, however, and the only criterion is that the pressure be sufficiently great to ensure at least partial liquid phase. For olefins other than ethylene, the process disclosed herein may be practiced generally at a pressure of from 345 to 6985 kPa(g) (50 to 1000 psi(g)).

The weight hourly space velocity (WHSV) of the feed olefin may range from 0.01 to 8.0 $hr^{-1}$. As used herein, weight hourly space velocity of a component means the weight flow rate of the component per hour divided by the catalyst weight, where the weight flow rate of the component per hour and the catalyst weight are in the same weight units. The WHSV of aromatics, including benzene and a polyalkylaromatic having at least two $C_2^+$ groups, if any, is generally from 0.3 to 480 $hr^{-1}$. In a preferred embodiment, in which the polyalkyl aromatic is a diethylbenzene or a triethylbenzene, the molar ratio of benzene per ethylene is from 1.5:1 to 6:1, the WHSV of ethylene is from 0.1 to 6.0 $hr^{-1}$, and the WHSV of aromatics including benzene and the polyethylbenzenes is from 0.5 to 70 $hr^{-1}$.

EXAMPLES

As synthesized UZM-8 of $Si/Al_2$ molar ratio of about 20 is prepared as per the following method. In a large beaker, 160.16 grams of diethyldimethylammonium hydroxide is added to 1006.69 grams de-ionized water, followed by 2.79 grams of 50 wt % NaOH solution. Next, 51.48 grams of liquid sodium aluminate is added slowly and stirred for 20 minutes. Then, 178.89 grams of $SiO_2$ (sold in commerce as Ultrasil) is slowly added to the gel and stirred for 20 minutes. Next, 24 grams of UZM-8 seed is added to the gel, and stirred for an additional 20 minutes. The gel is then transferred to a 2-liter stirred reactor and heated to 160° C. in 2 hours and subsequently crystallized for 115 hours. After digestion, the material is filtered and washed with de-ionized water and dried at 100° C. XRD (X-Ray Diffraction) analysis of the resulting material shows pure UZM-8. The elemental analysis by inductively coupled plasma-atomic emission spectroscopy (ICP-AES) shows a $Si/Al_2$ molar ratio of 20.

Example 1 is a comparative example that is made of 70 wt % UZM-8 and 30 wt % alumina. In preparing the catalyst, the as synthesized UZM-8 is first mixed and mulled with $HNO_3$ peptized Catapal C alumina (made using a $HNO_3$ to alumina weight ratio of 0.17) to attain dough consistency readily to be extruded into pellets of a cylindrical shape of 1/16" diameter. The extrudate was calcined at 600° C. in flowing air for about 1 hour. The calcined catalyst was then ammonium ion exchanged to remove sodium using 10 wt % ammonium nitrate solution at a dosage of 1 gram ammonium nitrate per gram of calcined catalyst at about 60° C.

Example 2 is also a comparative example that is made in the same manner as example 1 with the exception that it contains 50 wt % UZM-8 and 50 wt % alumina in a trilobed shape of 1/16" circumference.

Examples 3 and 4 represent those used in this invention, and contain 30 and 12 wt % UZM-8 zeolite, respectively, with the balance being alumina in a trilobed shape of 1/16" circumference.

To test the catalyst performance, 25 grams of catalyst was mixed with quartz sand to fill the interstitial voids to ensure proper flow distribution before being loaded into a 7/8" ID standard steel reactor. The catalyst was dried down with flowing benzene pretreated using 3 A dryer at 200° C. for 12 hours. After the drydown, the recycle benzene was introduced followed by propylene. The benzene to propylene molar ratio for the test was targeted at 2.0, with a product effluent to combined fresh feed ratio of 7.4 on a weight basis, propylene weight hourly space velocity of 1.04 $hr^{-1}$, an inlet temperature of 115° C., and an outlet pressure of 3549 kPa (500 psig). The product effluent was monitored by on-line GC. The performance of catalyst examples 1 through 4 is summarized in the following table. The catalyst activity measured by olefin conversions across the reactor is consistently near 100% and shows no indication of lowered activity with reduced zeolite contents from 70 to 12 wt %. Furthermore, the total alkylated product selectivity is consistently close to 100%, even at very low zeolite contents under very severe but economic process conditions of a benzene to olefin molar ratio of 2.0 and an inlet temperature of 115° C.

TABLE 1

| Examples | UZM-8 Zeolite % | % C3= Conversion | total alkylated selectivity, % | Size of Active Zone, inches | % active zone |
|---|---|---|---|---|---|
| #1 | 70 | 99.8 | 99.76 | 1.75 | 28 |
| #2 | 50 | 99.86 | 99.7 | 2.5 | 41 |
| #3 | 30 | 99.86 | 99.75 | 1.5 | 27 |
| #4 | 12 | 99.87 | 99.75 | 1.75 | 37 |

The catalyst activity measured by the size of the active zone is summarized in FIG. 1. It is unexpected to discover that the size of the active zone going from 70 to 12 wt % zeolite stays relatively constant and the variability is within the reproducibility of catalyst bed locations.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for alkylation of feedstock comprising:
   contacting the feedstock comprising at least one alkylatable aromatic compound and an alkylating agent with a first alkylating catalyst composition under alkylating conditions including at least a temperature of from about 90° C. to about 230° C. and a molar ratio of alkylatable aromatic compound to alkylating agent of from about 1 to 3, the first alkylating catalyst composition comprising UZM-8zeolite and a binder, the first alkylating catalyst composition having less than about 5wt % UZM-8zeolite;
   wherein a total alkylated selectivity at the temperature of from about 90° C. to about 230° C. and the molar ratio of alkylatable aromatic compound to alkylating agent of from about 1 to about 3 is greater than 99.0%, a conversion of the alkylating agent is greater than 90%, and an active zone in a catalyst bed containing the first alkylating catalyst is no more than about 50% of a total length of the catalyst bed.

2. The method of claim 1 wherein the first alkylating catalyst composition has about 2wt % to less than about 5wt % UZM-8zeolite.

3. The method of claim 1 further comprising contacting the feedstock with at least one additional catalyst composition before contacting the feedstock with the first alkylating catalyst composition, the at least one additional catalyst composition capable of reacting with one or more of nitrogen, oxygenate species, sulfur, or metals, to reduce a level of nitrogen, oxygen, sulfur, or metals in the feedstock.

4. The method of claim 1 further comprising contacting the feedstock with a second alkylating catalyst composition after contacting the feedstock with the first alkylating catalyst composition, the second alkylating catalyst composition comprising a zeolite and a binder, the second alkylating catalyst composition having greater than 50wt % zeolite.

5. The method of claim 1 wherein the alkylating conditions include a pressure of from about 1.3 MPa to about 4.8 MPa, and a feed hourly weight space velocity based on the alkylating agent of from about 0.5 to about 10 $hr^{-1}$.

6. The method of claim 1 wherein the alkylatable aromatic compound is benzene, the alkylating agent is propylene, and the propylene conversion is greater than 95%.

7. The method of claim 1 wherein the alkylatable aromatic compound is benzene, the alkylating agent is propylene, and the propylene conversion is greater than 97%.

8. The method of claim 1 wherein the alkylatable aromatic compound is benzene, the alkylating agent is ethylene, and the ethylene conversion is greater than 95%.

9. The method of claim 1 wherein the alkylatable aromatic compound is benzene, the alkylating agent is ethylene, and the ethylene conversion is greater than 97%.

10. The method of claim 1 wherein the alkylatable aromatic compound is benzene, the alkylating agent is butene, and the butene conversion is greater than 95%.

11. The method of claim 1 wherein the alkylatable aromatic compound is benzene, the alkylating agent is butene, and the butene conversion is greater than 97%.

12. A method for alkylation of feedstock comprising:
   contacting the feedstock comprising at least one alkylatable aromatic compound and an alkylating agent with at least one additional catalyst composition, the at least one additional catalyst composition capable of reacting with one or more of nitrogen, oxygen, sulfur, or metals, forming a feedstock having a reduced level of nitrogen, oxygen, sulfur, or metals;
   contacting the feedstock with the reduced level of nitrogen, oxygen, sulfur, or metals with a first alkylating catalyst composition under alkylating conditions including at least a temperature of from about 90° C. to about 230° C. and a molar ratio of alkylatable aromatic compound to alkylating agent of from about 1 to 3, the first alkylating catalyst composition comprising UZM-8zeolite and a binder, the first alkylating catalyst composition having less than about 5 wt % UZM-8zeolite;

wherein a total alkylated selectivity at the temperature of from about 90° C. to about 230° C. and the molar ratio of alkylatable aromatic compound to alkylating agent of from about 1 to about 3 is greater than 99.0%, a conversion of the alkylating agent is greater than 90%, and an active zone in a catalyst bed containing the first alkylating catalyst is no more than about 50% of a total length length of the catalyst bed.

13. The method of claim 12 wherein the first alkylating catalyst composition has about 2 wt % to less than about 5 wt % UZM-8zeolite.

14. The method of claim 12 further comprising contacting the feedstock with a second alkylating catalyst composition after contacting the feedstock with the first alkylating catalyst composition, the second alkylating catalyst composition comprising a zeolite and a binder, the second alkylating catalyst composition having greater than 50 wt % zeolite.

15. The method of claim 12 wherein the alkylating conditions include a pressure of from about 1.3 MPa to about 4.8 MPa, and a feed hourly weight space velocity based on the alkylating agent of from about 0.5 to about 10 hr$^{-1}$.

16. The method of claim 12 wherein the alkylatable aromatic compound is benzene, the alkylating agent is propylene, ethylene, or butene, and the propylene, ethylene, or butene conversion is greater than 95%.

* * * * *